United States Patent
Olson

(10) Patent No.: US 8,292,940 B2
(45) Date of Patent: Oct. 23, 2012

(54) MEDICAL DEVICE HAVING A ROTATABLE SHAFT

(75) Inventor: Richard Olson, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 489 days.

(21) Appl. No.: 12/369,711

(22) Filed: Feb. 11, 2009

(65) Prior Publication Data

US 2010/0204771 A1    Aug. 12, 2010

(51) Int. Cl.
*A61F 2/06* (2006.01)

(52) U.S. Cl. ...................................... 623/1.11

(58) Field of Classification Search .................. 623/1.11, 623/1.12, 1.23; 606/108, 191–195; 604/533–536
See application file for complete search history.

(56) References Cited

U.S. PATENT DOCUMENTS

| | | | |
|---|---|---|---|
| 4,906,244 A | 3/1990 | Pinchuk et al. | |
| 5,397,305 A | 3/1995 | Kawula et al. | |
| 5,500,181 A | 3/1996 | Wang et al. | |
| 5,697,948 A | 12/1997 | Marin et al. | |
| 5,749,825 A | 5/1998 | Fischell et al. | |
| 5,855,565 A | 1/1999 | Bar-Cohen et al. | |
| 6,290,673 B1 | 9/2001 | Shanley | |
| 6,299,595 B1 * | 10/2001 | Dutta et al. | 604/96.01 |
| 6,471,672 B1 | 10/2002 | Brown et al. | |
| 6,514,237 B1 | 2/2003 | Maseda | |
| 6,540,719 B2 | 4/2003 | Bigus et al. | |
| 6,589,251 B2 | 7/2003 | Yee et al. | |
| 6,599,315 B2 | 7/2003 | Wilson | |
| 6,752,433 B2 | 6/2004 | Frost | |
| 7,314,480 B2 | 1/2008 | Eidenschink et al. | |
| 2002/0072755 A1 | 6/2002 | Bigus et al. | |
| 2003/0055483 A1 | 3/2003 | Gumm | |
| 2004/0041395 A1 * | 3/2004 | Frost | 285/98 |
| 2005/0165439 A1 | 7/2005 | Weber et al. | |

(Continued)

FOREIGN PATENT DOCUMENTS

| | | |
|---|---|---|
| WO | 03017872 | 3/2003 |
| WO | 2006/020457 A1 | 2/2006 |
| WO | 2008/113372 A1 | 9/2008 |

OTHER PUBLICATIONS

Bar-Cohen et al., "Electro-Active Polymer (EAP) Actuators for Planetary Applications," Proceeding of SPIE Annual International Symposium on Smart Structures and Materials, SPIE, Paper No. 3669-05, Newport Beach, CA, pp. 57-63, Mar. 1999.

(Continued)

*Primary Examiner* — Katherine Dowe
(74) *Attorney, Agent, or Firm* — Seager, Tufte & Wickhem, LLC

(57) ABSTRACT

The invention provides design, material, manufacturing method, and use alternatives for medical devices. An example medical device includes a first elongated member having a proximal end, a distal end, and a lumen extending therebetween and a second elongated member having a proximal end, a distal end, and a lumen extending therebetween. The proximal end of the second elongated member may be disposed adjacent to the distal end of the first elongated member forming an actuatable junction. In some cases, the actuatable junction may be actuatable between a first state and a second state. When in the first state, the first elongated member may be rotatable relative to the second elongated member and, when in the second state, the first elongated member may be fluidly sealed to the second elongated member.

21 Claims, 8 Drawing Sheets

U.S. PATENT DOCUMENTS

2005/0182473 A1* 8/2005 Eidenschink et al. ....... 623/1.11
2005/0187602 A1  8/2005 Eidenschink
2005/0187603 A1* 8/2005 Eidenschink et al. ....... 623/1.11
2006/0206188 A1  9/2006 Weber et al.
2008/0027377 A1  1/2008 Alkhatib et al.

OTHER PUBLICATIONS

U.S. Appl. No. 12/199,563, filed Aug. 27, 2008, to Harrison.

* cited by examiner

MEDICAL DEVICE HAVING A ROTATABLE SHAFT

FIELD OF THE INVENTION

The present invention relates generally to medical devices and, more particularly, to intracorporal medical device, such as a guidewire, catheter, or the like having a rotatable shaft.

BACKGROUND

The use of intravascular medical devices has become an effective method for treating many types of vascular disease. In general, one or more suitable intravascular devices are inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular devices include percutaneous transluminal angioplasty (PTA) and percutaneous transluminal coronary angioplasty (PTCA).

When in use, intravascular devices, such as a catheter, may enter the patient's vasculature at a convenient location and then can be advanced over a guidewire to a target region in the anatomy. The path taken within the anatomy of a patient may be very tortuous, and as such, it may be desirable to combine a number of performance features in the intravascular device to aid in advancing the catheter over the guidewire. For example, it is sometimes desirable that the catheter have a relatively high level of pushability and torqueability. It is also sometimes desirable that a catheter be relatively flexible, for example, to aid in advancing the catheter over the guidewire to access a treatment site. In addition, for some applications, catheters may also be expected to exhibit tensile and/or compressive strength in certain regions.

A number of different elongated medical device structures, assemblies, and methods are known, each having certain advantages and disadvantages. However, there is an ongoing need to provide alternative elongated medical device structures, assemblies, and methods. In particular, there is an ongoing need to provide alternative medical devices including structure or assemblies configured to aid in advancing a catheter over a guidewire in a vessel of a patient, and methods of making and using such structures and/or assemblies.

BRIEF SUMMARY

The invention provides design, material, manufacturing method, and use alternatives for medical devices. An example medical device includes a first elongated member having a proximal end, a distal end, and a lumen extending therebetween and a second elongated member having a proximal end, a distal end, and a lumen extending therebetween. The proximal end of the second elongated member may be disposed adjacent to the distal end of the first elongated member forming an actuatable junction. In some cases, the actuatable junction may be actuatable between a first state and a second state. When in the first state, the first elongated member may be rotatable relative to the second elongated member and, when in the second state, the first elongated member may be fluidly sealed and/or rotationally fixed relative to the second elongated member.

In some embodiments, a seal may be disposed adjacent to the first elongated member and the second elongated member at the actuatable junction. In some cases, the seal may be actuatable between a first state where the junction is fluidly sealed and a second state where the junction is not fluidly sealed.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
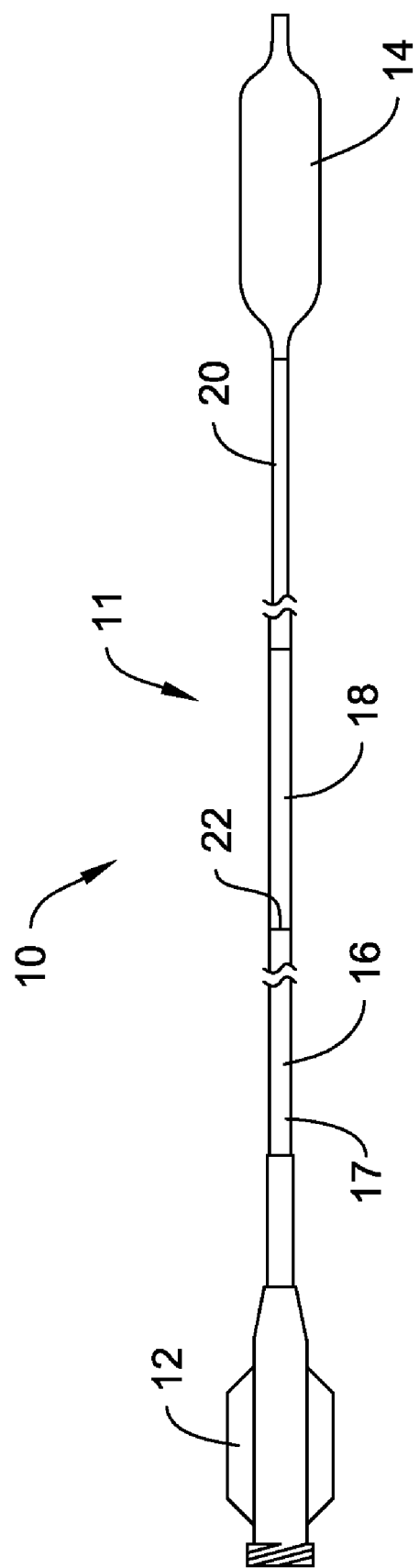
FIG. 1 is a perspective view of an illustrative embodiment of a balloon catheter.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an" and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a perspective view of an illustrative embodiment of a balloon catheter 10. In the illustrative embodiment, the balloon catheter 10 may include an elongated shaft 11 having a proximal end, a distal end, and one or more lumens extending therebetween. In the illustrative example, the one or more lumens may include an inflation lumen, a guidewire lumen, or any other lumen, as desired. An inflatable balloon 14 may be disposed adjacent to the distal end of the elongated shaft 11. In some cases, the balloon 14 may be a typical angioplasty, stent delivery, or other inflatable member, as desired. A hub assembly 12 may be connected to the proximal end of the elongated shaft 11 to facilitate connection to an inflation device for inflating/deflating the balloon 14, and/or to facilitate insertion of a guidewire or other medical device therein. In some cases the inflatable balloon 14 may be fluidly connected to the hub assembly 12 via an inflation lumen of the elongated shaft 11.

In the illustrative embodiment, the elongated shaft 11 may include a proximal section 16, a midshaft section 18, and a distal section 20. In the illustrative embodiment, a distal end of the proximal section 16 may be disposed adjacent to and/or connected to a proximal end of the midshaft section 18 forming an actuatable junction 22. Furthermore, it is contemplated that the actuatable junction 22 may be provided between a distal end of the midshaft 18 and a proximal end of the distal section 20, or in any other suitable location along the length of the elongated shaft 11, as desired.

In some cases, the actuatable junction 22 may be actuatable between a rotatable state (i.e. midshaft section 18 rotatable relative to the proximal section 16) and a non-rotatable state (i.e. midshaft section 18 rotatably fixed relative to the proximal section 16). Additionally or alternatively, the actuatable junction 22 may be actuatable between a non-fluidly sealed state and a fluidly sealed state. In some cases, the non-fluidly sealed state of the junction 22 may be a rotatable state and the fluidly sealed state of the junction 22 may be a rotatable state or a non-rotatable state, as desired. In some cases, the actuatable junction 22 may be actuatable according to an electrical potential, a pressure source, or any other suitable actuation means, as desired.

In the illustrative example, the proximal section 16 of the elongated shaft 11 may include an elongated tubular member having a lumen extending therethrough. In one example, the proximal section 16 of the elongated shaft 11 may include a hypotube 17. In some cases, the hypotube 17 may include one or more openings, slits, or other features to achieve a desired stiffness and flexibility, as desired. In some embodiments, the hypotube 17 may include a material to impart flexibility and stiffness characteristics according to the desired application. In the illustrative embodiment, the hypotube 17 may include a material to impart stiffness and pushability in the catheter 10. For example, the hypotube 17 may include a rigid and resilient material. In such an embodiment, the hypotube 17 may be made from a metal, a metal alloy, a polymer, a metal-polymer composite, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®, and the like), other nickel-chromium alloys, other nickel-molybdenum alloys, other nickel-cobalt alloys, other nickel-iron alloys, other nickel-copper alloys, other nickel-tungsten or tungsten alloys, and the like; cobalt alloys, such as cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material. However, this is not meant to be limiting and it is to be understood that the hypotube 17 may include any suitable material described herein with reference to any other catheter component, such as, for example, a polymer or polymer blend discussed below, or any suitable material commonly used in medical devices, as desired. Furthermore, it is to be understood that any suitable catheter component may be used in the proximal section 16 of the catheter 10 and it is not limited to be a hypotube 17, as desired.

In the illustrative embodiment, a distal end of the proximal section 16 may be coupled to or otherwise connected to a proximal end of the midshaft section 18, such as, for example, at the actuatable junction 22. The midshaft section 18 may include a tubular member including a proximal end disposed adjacent to the distal end of the hypotube 17, a distal end, and one or more lumens extending therethrough. There are numerous materials that can be used for the midshaft of catheter 10 to achieve the desired properties that are commonly associated with medical devices. Some example materials can include, but is not limited to, stainless steel, metal, nickel alloy, nickel-titanium alloy, hollow cylindrical stock, thermoplastics, high performance engineering resins, polymers, fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro (propyl vinyl ether) (PFA), polyoxymethylene (POM), polybutylene terephthalate (PBT), polyether block ester, or other polymer blends. For example, the polymer blend may include polyoxymethylene blended with a polyether polyester such as ARNITEL® available from DSM Engineering Plastics or HYTREL® available from DuPont. Other suitable polymers that may be blended with polyoxymethylene include polyether block ester, polyether block amide (PEBA, for example available under the trade name PEBAX®), polyetheretherketone (PEEK), polyetherimide (PEI), and the like. A suitable polyoxymethylene is commercially available under the trade name Delrin™ commercially available from DuPont Wilmington, Del. In some cases, the midshaft section 18 is manufactured so as to maintain the desired level of stiffness, flexibility, and torqueability according to multiple embodiments of the current invention and includes multiple layers over at least portions of its length which provide selected flexibility. However, it is to be understood that the above mentioned materials are not meant to be limiting and it is to be understood that the midshaft 18 may include any suitable material described herein with reference to any other catheter component or any suitable material commonly used in medical devices, as desired.

In the illustrative embodiment, the distal section 20 of the elongate shaft 11 may be disposed distally of the midshaft section 18. For example, the distal section 20 may include a proximal end disposed adjacent to the distal end of the midshaft section 18, a distal end, and one or more lumens extending therethrough. In some cases, the inflatable balloon 14 may be disposed about at least a portion of the distal section 20 adjacent to the distal end. The distal section 20 may include those materials that are commonly used in medical devices. Some example materials can include, but is not limited to, stainless steel, metal, nickel alloy, nickel-titanium alloy, hollow cylindrical stock, thermoplastics, high performance engineering resins, polymers, fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro (propyl vinyl ether) (PFA), polyoxymethylene (POM), polybutylene terephthalate (PBT), polyether block ester, or other polymer blends. For example, the polymer blend may include polyoxymethylene blended with a polyether polyester such as ARNITEL® available from DSM Engineering Plastics or HYTREL® available from DuPont. Other suitable polymers that may be blended with polyoxymethylene include polyether block ester, polyether block amide (PEBA, for example available under the trade name PEBAX®), polyetheretherketone (PEEK), polyetherimide (PEI), and the like. A suitable polyoxymethylene is commercially available under the trade name Delrin™ commercially available from DuPont Wilmington, Del. In some cases, the distal section 20 is manufactured so as to maintain the desired level of stiffness, flexibility, and torqueability according to multiple embodiments of the current invention and includes multiple layers over at least portions of its length which provide selected flexibility. However, this is not meant to be limiting and it is to be understood that the distal section 20 may include any suitable material described herein with reference to any other catheter component or any suitable material commonly used in medical devices, as desired.

Furthermore, it should be understood that other suitable structures or components, may be incorporated into the elongate shaft 11 of the catheter 10. For example, a braided member, one or more coils, and/or marker members, or the like may be disposed along a portion of or the entire length of the elongated shaft 11. In example cases when a braided member is provided, the braided member may be provided in the proximal section 16, in the midshaft 18, in the distal section 20, or any combination thereof, as desired. The braided member may take on a number of forms. Typically the braided member will include a lubricious inner layer and a polymeric outer layer, with a braid composed of a number of filaments or strands braided between the inner and outer layers. A helical, double helical, coiled, or woven member may be used in place of the braid, if desired.

Figure 2:
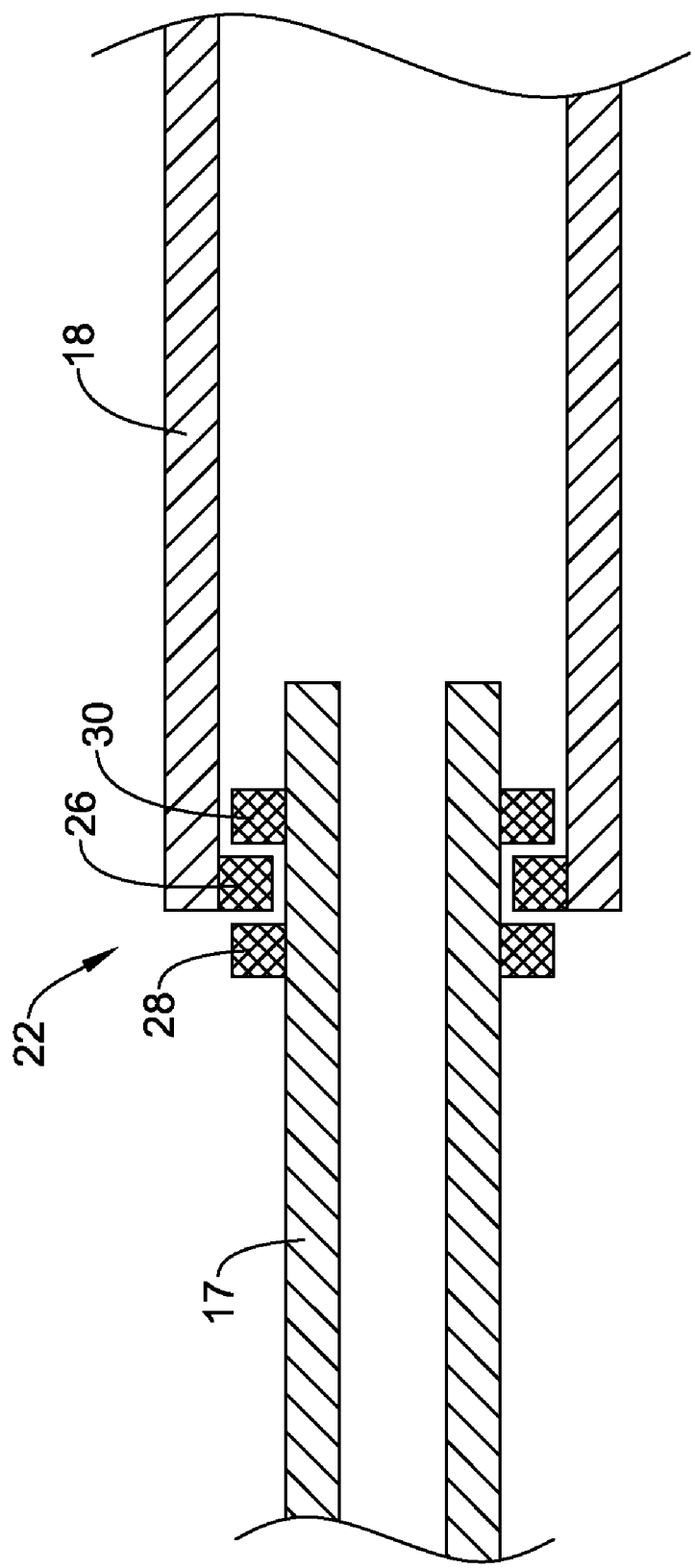
FIG. 2 is a partial cross-sectional view of an illustrative junction for the catheter embodiment of FIG. 1.

FIG. 2 is a partial cross-sectional view of an illustrative actuatable junction 22 for the catheter embodiment of FIG. 1. In the illustrative embodiment, the actuatable junction 22 may couple or otherwise connect the distal end of the hypotube 17 to the proximal end of the midshaft 18. In the illustrative example, the midshaft 18 may include a lumen having a diameter that is relatively greater than the outer diameter of the hypotube 17. In this configuration, the distal end of the hypotube 17 may be at least partially disposed within the lumen of the midshaft 18. However, this is not meant to be limiting in any manner. It is contemplated that the midshaft section 18 and the hypotube may have substantially similar diameters or the mid shaft section 18 may include an outer surface have a diameter relatively smaller than a diameter of the lumen of the hypotube 17, as desired.

In the illustrative embodiment, one or more retainers 26, 28, and 30 may be disposed in at least a portion of the actuatable junction 22. In some cases, the one or more retainers 26, 28, and 30 may form a seal. In the example embodiment, retainers 28 and 30 may be disposed about at least a portion of the outer surface of the hypotube 17 and retainer 26 may be disposed on an inner surface of the midshaft section 18 within the lumen. In some cases, the retainers 26, 28, and 30 may be a retaining ring or other suitable annular shaped retainer, as desired. However, it is contemplated that any suitable retainer may be used, as desired.

In the illustrative embodiment, the retainers 26, 28, and 30 may be configured and/or arranged to limit longitudinal movement of the hypotube 17 relative to the midshaft 18. As shown, retainer 28 may limit proximal movement of the midshaft section 18 relative to the hypotube 17 and retainer 30 may limit distal movement of midshaft section 18 relative to the hypotube 17. Additionally, in this illustrative configuration, the retainers 26, 28, and 30 may allow rotational movement of the hypotube 17 relative to the midshaft 18. As illustrated, the illustrative actuatable junction 22 may include a gap between the retainer 26 and the outer surface of the hypotube 17 and a gap between retainer 26 and both retainers 28 and 30. In this illustrative configuration, the actuatable junction 22 may not be fluidly sealed. However, it is contemplated that the actuatable junction 22 may be manipulated to be fluidly sealed and allow rotation of the hypotube 17 relative to the midshaft 18, as desired.

Figure 3:
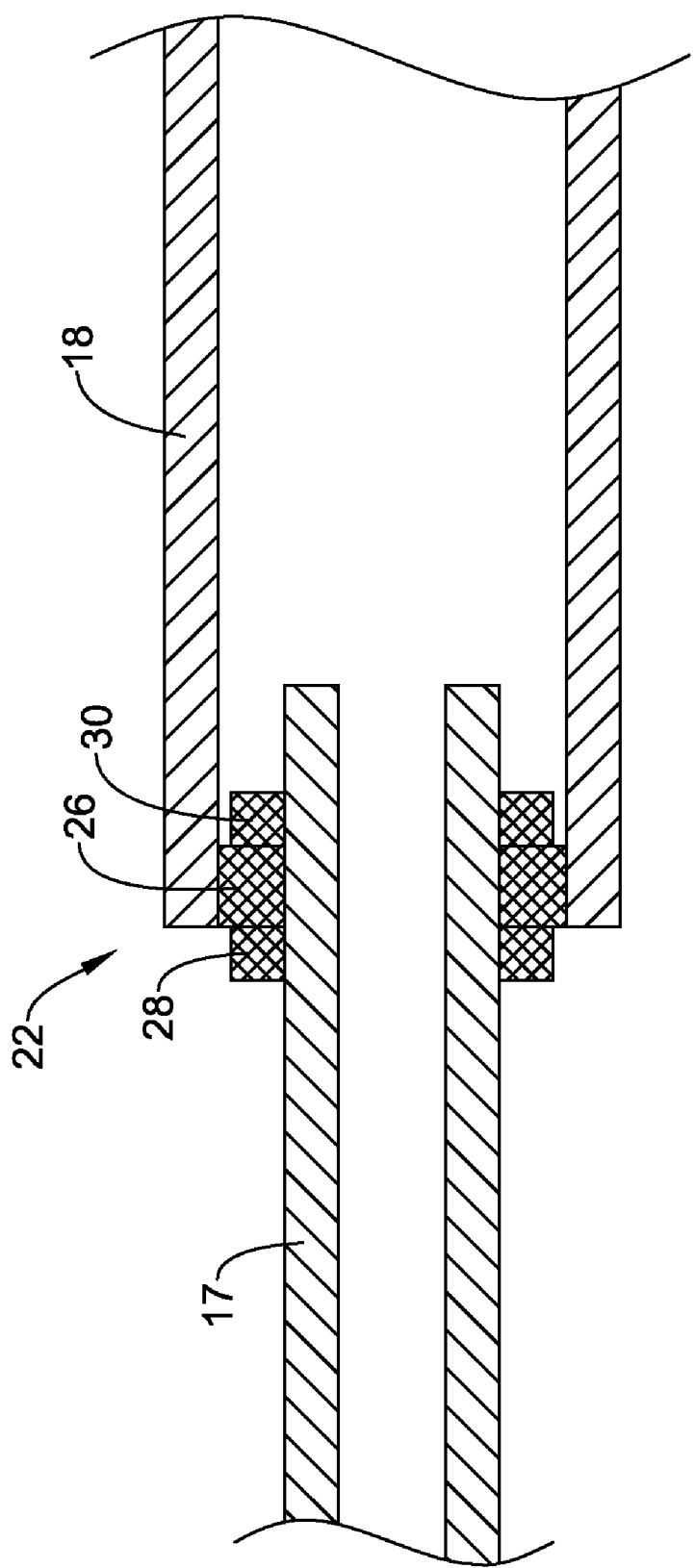
FIGS. 3 and 4 are partial cross-sectional views of example embodiments of the junction of FIG. 2.

FIG. 3 is a partial cross-sectional view of an example embodiment of the actuatable junction 22 of FIG. 2. In the illustrative embodiment, the retainer 26 may be actuated to be in a fluidly sealed and/or non-rotatable state, at least in part, by using an electroactive polymer (EAP) actuator. EAPs are polymers that are characterized by their ability to change shape in response to an electrical stimulus. For example, in some embodiments the EAP material may expand about 0.5% to about 20% when exposed to an electric current of 0.001 microAmps to 1 milliAmps (−2 to +2 V). Some examples of materials that may be used in EAPs may include, but is not limited to, polypyrroles, polyanilines, polythiophenes, polyethylenedioxythiophenes, poly(p-phenylene vinylene)s, polysulfones, polyacetylenes, Nafion, Bucky paper and any other ionic electro-active polymer that is considered to have low voltage, low speed, high stress (up to 500 MPa), characteristics. Furthermore, it is contemplated that any electroactive polymer that exhibits contractile or expansile properties may be used in connection with the various active regions of the invention, including those listed above.

These EAPs may have a number of properties that make them attractive for use in the medical devices such as, for example, they are lightweight, flexible, small and easily manufactured; energy sources are available which are easy to control, and energy can be easily delivered to the EAPS; small changes in potential (e.g., potential changes on the order of 1V) can be used to effect volume change in the EAPs; they are relatively fast in actuation (e.g., full expansion/contraction in a few seconds); EAP regions can be created using a variety of techniques, for example, electrodeposition; EAP regions can be patterned, for example, using photolithography; and many other properties. EAP materials and some of their notable characteristics are described in an article entitled Electro-Active Polymer Actuators for Planetary Applications by Y. Bar-Cohen et al. and published in Paper No. 3669-05 of the Proceedings of SPIE Annual International Symposium on Smart Structures and Materials, March 1999, Newport Beach, Calif. SPIE Copyright 1999, the entire contents of which being incorporated herein by reference.

In many applications, EAPs generally utilize the following elements to bring about electroactive polymer actuation: a source of electrical potential, an active region that includes the electroactive polymer, a counter electrode, and an electrolyte in contact with both the active region and the counter electrode. In many medical device applications, the source of electrical potential may be a battery provided in the hub.

However, this is not meant to be limiting and it is contemplated that any suitable source of electrical potential may be used, as desired.

In some cases, the active region may be a polypyrrole-containing active region. Polypyrrole-containing active regions can be fabricated using a number of known techniques, for example, extrusion, casting, dip coating, spin coating, or electro-polymerization/deposition techniques. Polypyrrole-containing active regions can also be patterned, for example, using lithographic techniques, if desired.

The counter electrode (not shown) may be formed from any suitable electrical conductive material or materials and is preferably biocompatible. For example, a conducting polymer, a conducting gel, or a metal, such as stainless steel, gold, silver, platinum, nitinol, or any other conductive metal, as desired. At least a portion of the surface of the counter electrode is generally in contact with the electrolyte, in order to provide a return path for charge.

The electrolyte (not shown), which may be in contact with at least a portion of the surface of the active region, allows for the flow of ions and thus acts as a source/sink for the ions. The electrolyte may be, for example, a liquid, a gel, or a solid, so long as ion movement is permitted. Where the electrolyte is a liquid, it may be, for example, an aqueous solution containing a salt, for example, an NaCl solution, a KCl solution, a sodium dodecylbenzene sulfonate solution, a phosphate buffered solution, physiological fluid, and so forth. Where the electrolyte is a gel, it may be, for example, a salt-containing agar gel or polymethylmethacrylate (PMMA) gel. Where the electrolyte is a solid, it may be, for example, a polymer electrolyte.

In some examples, the EAP may be configured to expand in at least one radial dimension (i.e., in at least one dimension that is orthogonal to the longitudinal axis of the device) upon activation of the active region. In other examples, the EAP may be configured to expand in at least one axial dimension (i.e. in at least one dimension parallel to the longitudinal axis of the device) upon activation of the active region. Furthermore, it is contemplated that the EAP may be configured to expand in at least one radial dimension and at least one axial dimension upon activation of the active region, as desired. Furthermore, upon the deactivation of the active region (i.e. removal of electrical potential), the EAP may be configured to contract in the at least one radial dimension and/or at least one axial dimension. Some examples of suitable techniques, methods, and structures for EAPs are disclosed in application Ser. No. 10/763,825 titled "Electrically Actuated Medical Devices", which is hereby incorporated by reference.

In the illustrative embodiment, upon activation of the active region, or EAP, the retainer 26 may be configured to expand in a radial and/or an axial direction, as shown. In this activated state, retainer 26 may contact one or more of retainer 28, retainer 30, and hypotube 17. Upon contact, the retainer 26 may fluidly seal the actuatable junction 22. Additionally, in some cases, the contact may inhibit and/or prevent rotation of the hypotube 17 relative to the midshaft 18, if desired. In some cases, the retainer 26 may cause a friction fit with retainer 28, retainer 30, and/or hypotube 17.

In the illustrative embodiment, the retainer 26 including the EAP may be electrically connected to an electrical potential, such as, for example, a battery provided in the hub by an electrical conductor line (not shown). Example conductor lines are disclosed in application Ser. No. 12/199,563, entitled "Electrically Conductive Pathways in Medical Devices" filed on Aug. 27, 2008, which is hereby incorporated by reference.

Figure 4:
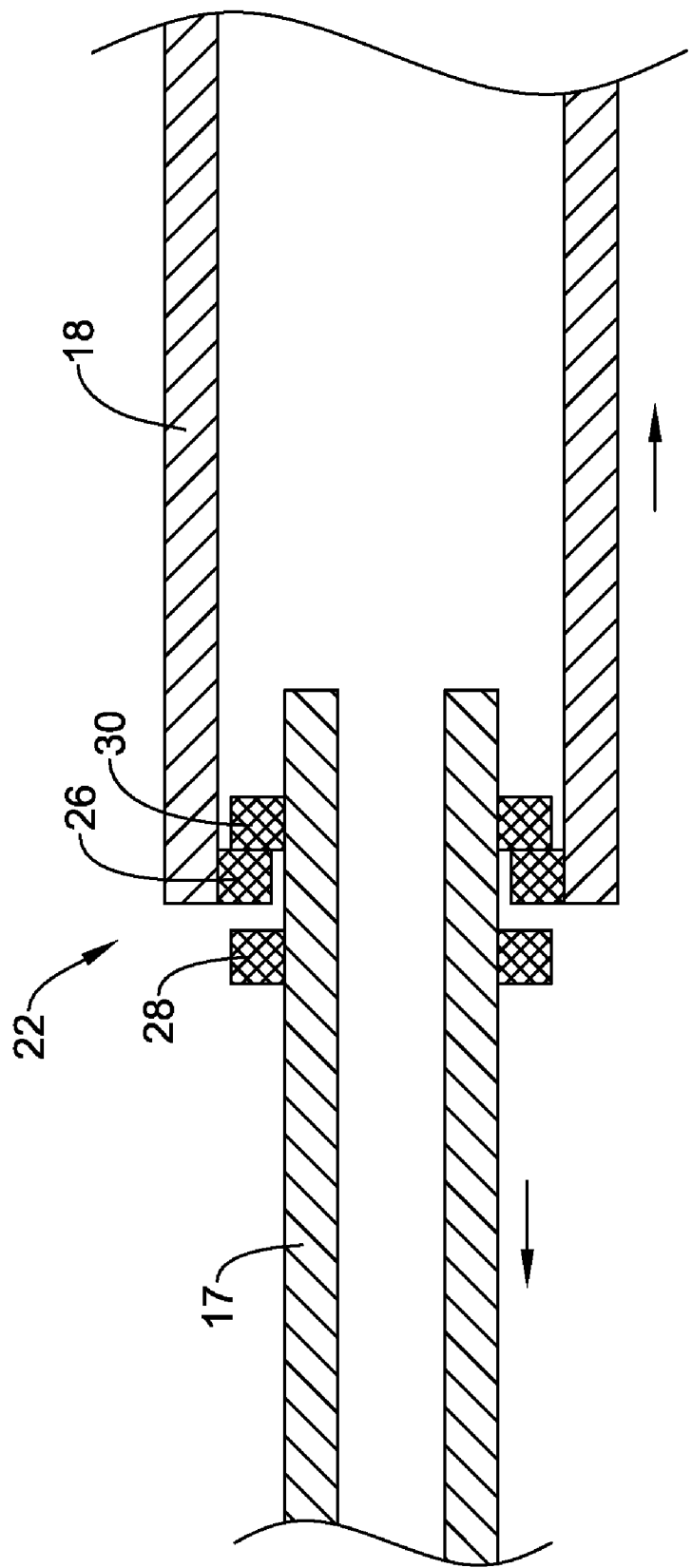

FIG. 4 is a partial cross-sectional view of an example embodiment of the actuatable junction 22 of FIG. 2. In the illustrative example, the actuatable junction 22 may be actuated, at least in part, by a pressure source. In some cases, the pressure source may be provided through the lumen of the hypotube 17 and/or midshaft section. In one example, a fluid provided in the lumen of the hypotube 17 and/or midshaft 18 to inflate the balloon disposed at the distal end of the catheter may serve as the pressure source. The fluid disposed in the lumen may create a relative increase in pressure causing the hypotube 17 and the midshaft 18 to expand in an axial or longitudinal direction. In this example, the midshaft section 18 may move in a distal direction relative to the hypotube 17 and/or the hypotube 17 may move in a proximal direction relative to the midshaft section 18, as indicated by the arrows. This relative movement may cause retainer 26 to contact with retainer 30, which may create a fluid tight seal. Also, in some cases, the contact of retainers 26 and 30 may decrease, inhibit, and/or prevent rotational movement of the midshaft 18 relative to the hypotube 17, but this is not required. Upon the removal of the pressure source in the lumen, hypotube 17 and midshaft 18 may return to the configuration shown in FIG. 2.

Furthermore, it is contemplated that the hypotube 17 and the midshaft section 18 may move in a direction opposite to that discussed above causing the retainer 26 to contact retainer 28, if desired. In this case, the retainers 26 and 28 may fluidly seal the junction and/or decrease, inhibit, and/or prevent rotational movement of the hypotube 17 relative to the midshaft section 18.

Figure 5:
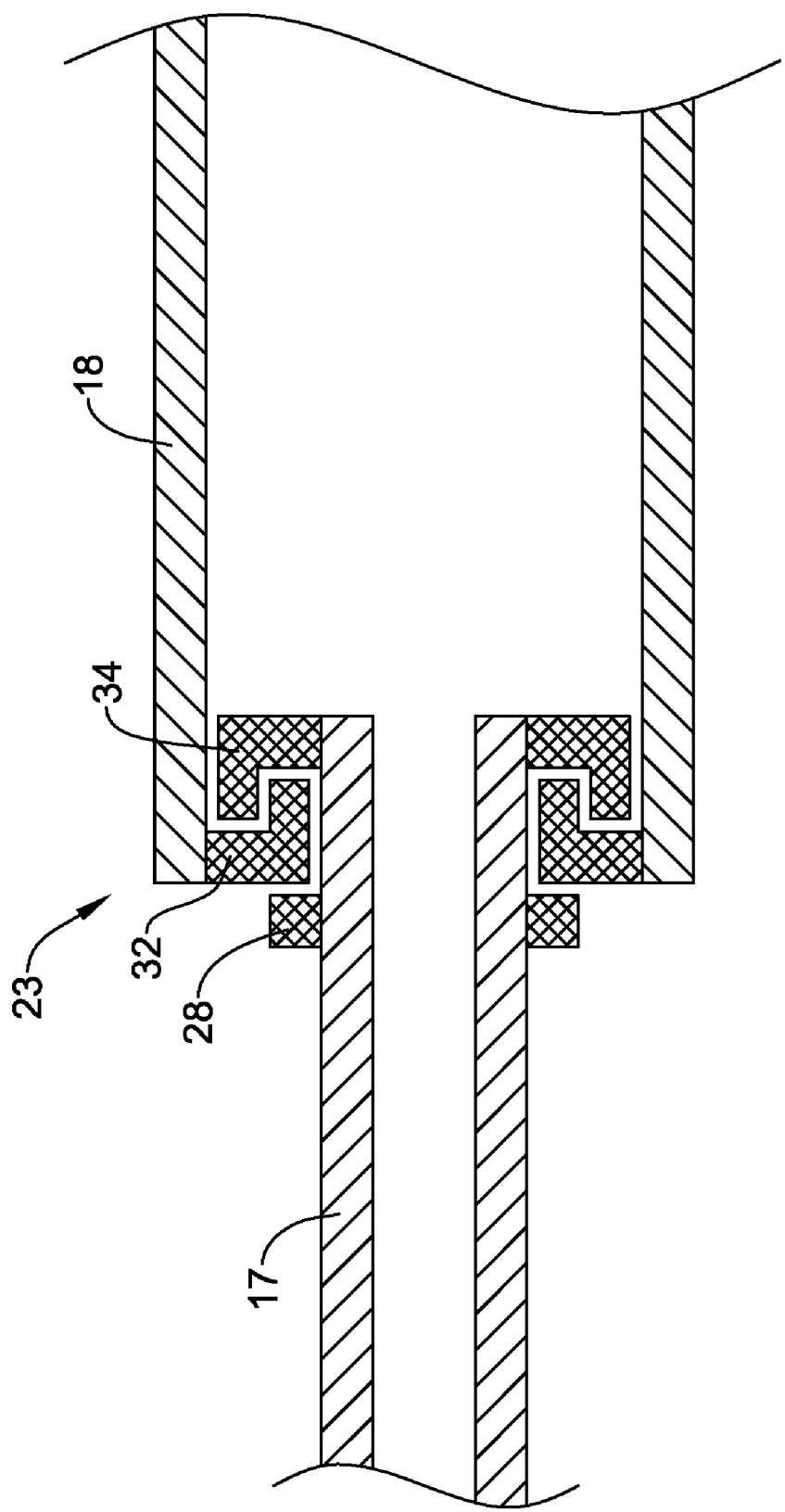
FIG. 5 is a partial cross-sectional view of an alternative illustrative junction of the catheter embodiment of FIG. 1.

FIG. 5 is a partial cross-sectional view of an alternative junction 23 of the catheter of FIG. 1. In the illustrative embodiment, the actuatable junction 23 may include one or more interlocking retainers 32 and 34. As illustrated, a first retainer 32 provided on the inside surface of the midshaft 18 in the lumen may be generally L-shaped. In some cases, retainer 32 may have an axially extending portion spaced a distance from the inner surface of the midshaft 18. A second retainer 34 may be provided on the outer surface of the hypotube 17 that may be configured to be generally L-shaped. In some cases, retainer 34 may have an axially extending portion spaced a distance from the outer surface of the hypotube 17. In this configuration, retainers 32 and 34 may be configured to interlock with one another when actuated. Similar to actuatable junction 22 of FIGS. 2-4, retainer 28 may limit proximal movement of the midshaft section 18 relative to the hypotube 17.

Figure 6:
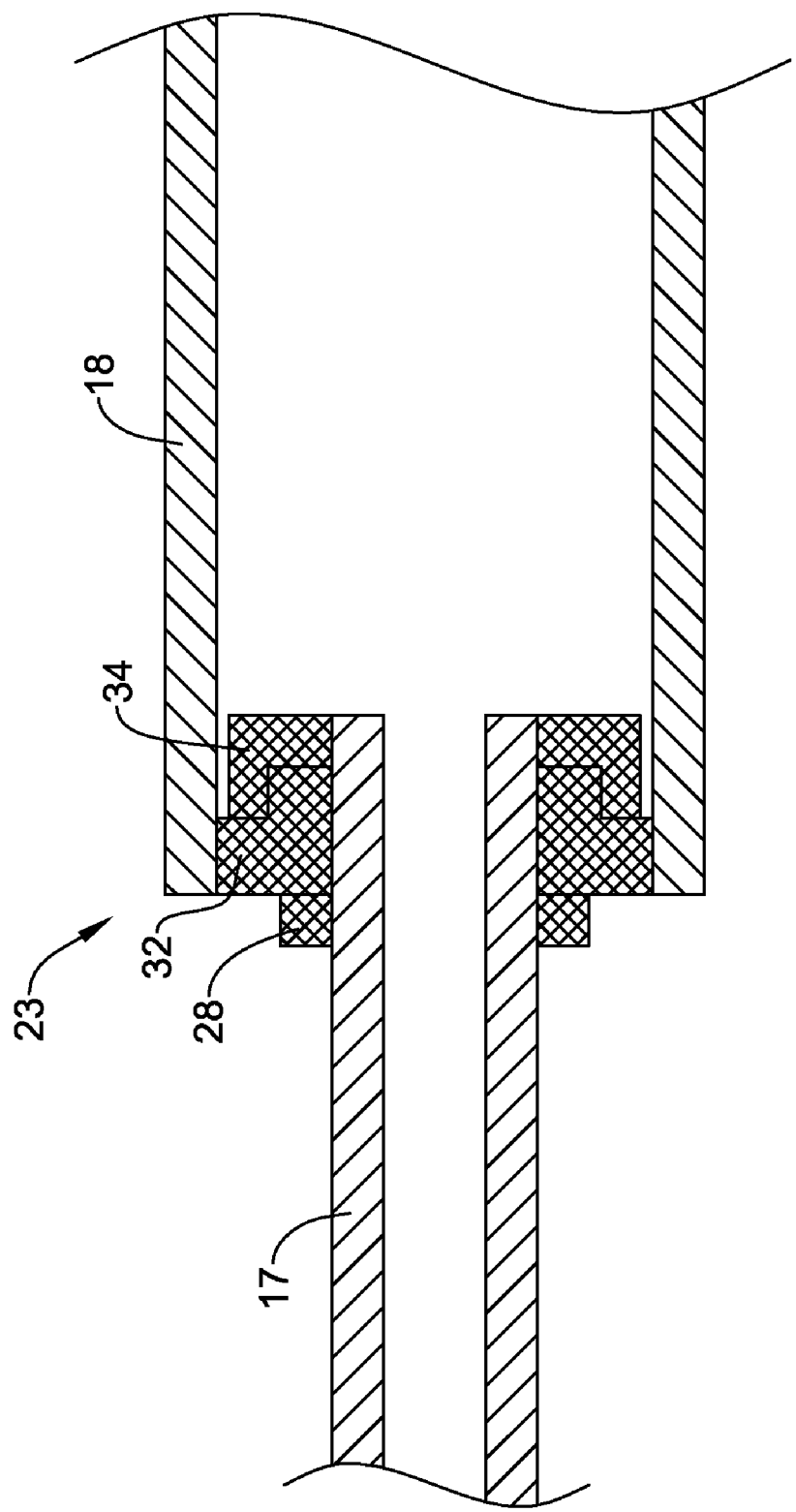
FIGS. 6 and 7 are partial cross-sectional views of example embodiments of the junction of FIG. 5.

FIG. 6 is a partial cross-sectional view of an illustrative example of the junction 23 of FIG. 5. In the illustrative example, the actuatable junction 23 may be actuated between a rotatable state and a non-rotatable state, and/or a fluidly sealed state and a non-fluidly sealed state, at least in part, by using an EAP. In some cases, the actuatable junction 23 may be actuated between a rotatable state and a fluidly sealed state, which may be rotatable or non-rotatable, as desired. As discussed previously, the EAP may be configured to expand when activated by an electrical potential. In the illustrative example, retainer 32 may include an EAP. However, it is contemplated that one or more of retainers 28, 32, and 34 may include an EAP, as desired.

As illustrated, retainer 32 is shown in an activated or expanded state with an electrical potential applied thereto. In this state, retainer 32 may be expanded in a radial dimension and/or an axial dimension, as desired. When expanded, retainer 32 may interlock with retainer 34 providing a fluid tight seal. In some cases, the interlocking of retainer 32 and 34 may also decrease, inhibit, and/or prevent rotation of the hypotube 17 relative to the midshaft 18. While the retainer 32 is shown as expanding in both the axial dimension and the radial dimension, it is contemplated that the EAP may be configured to expand in only one of the axial or radial dimensions, as desired.

Figure 7:
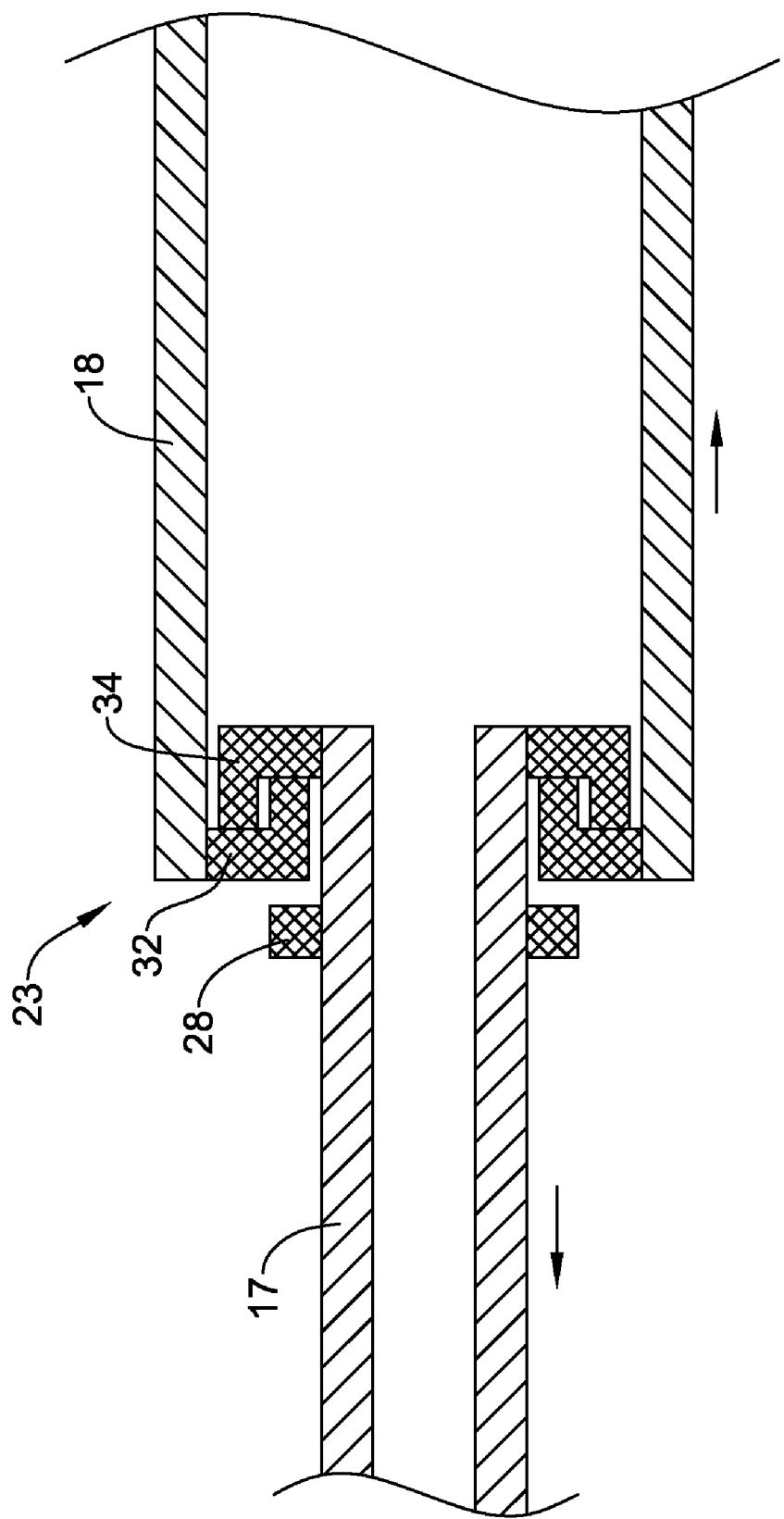

FIG. 7 is a partial cross-sectional view of an illustrative example of the actuatable junction 23 of FIG. 5. In the illustrative example, the actuatable junction 23 may be actuated, at least in part, by a pressure source. Similar to FIG. 4 discussed previously, when a pressure is introduced into the lumen of the hypotube 17 and/or the midshaft 18, the pressure may cause the midshaft 18 to move in an axial or longitudinal direction away from the hypotube 17 or the hypotube 17 may move in an axial or longitudinal direction away from the midshaft 18, as illustrated by the arrows. In some cases, this pressure may be from a fluid disposed through the lumen such as, for example, to inflate a balloon at the distal end of the catheter.

When activated, the interlocking retainers 32 and 34 may interlock with one another forming a fluid tight seal. In some cases, when activated, the retainers 32 and 34 may also decrease, inhibit, and/or prevent rotation of the midshaft 18 relative to the hypotube 17.

Figure 8:
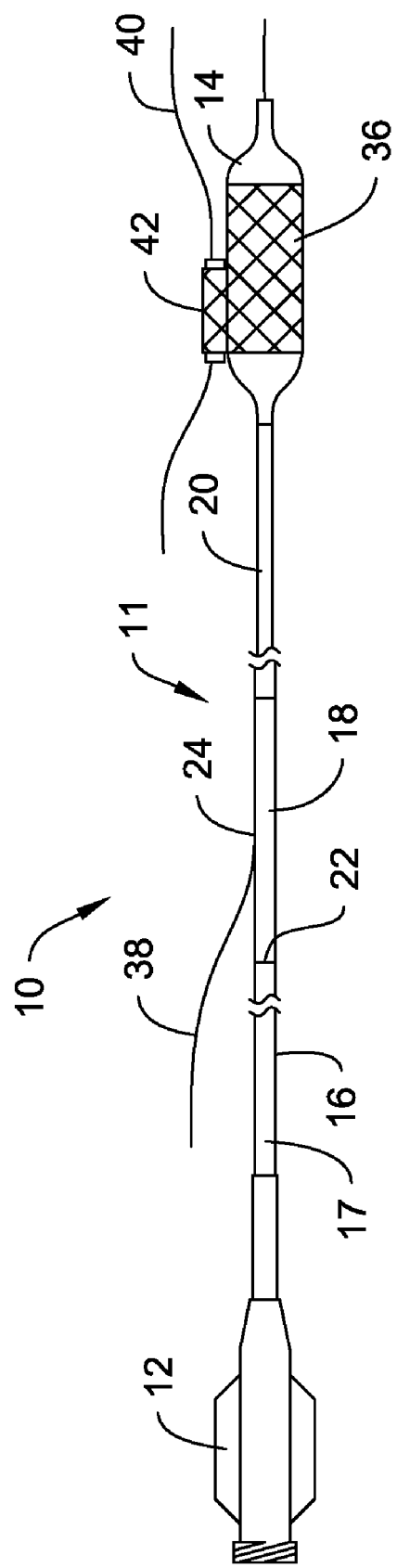
FIG. 8 is a schematic view of an illustrated balloon catheter including a stent.

FIG. 8 is a perspective view of an illustrative balloon catheter 10 including a stent 36. In the illustrative embodiment, the catheter 10 may include a secondary tubular member 42 including a secondary guidewire lumen configured to receive a second guidewire 40 therethrough. In some embodiments, the secondary tubular member 42 may be configured to engage a portion of the balloon 14. However, it is also contemplated that the secondary tubular member 42 may engage a portion of the elongated member 11, if desired. Although not illustrated, in some cases, it is contemplated that two or more secondary tubular members 42 may engage a portion of the balloon 42. In this case, the two or more secondary tubular members 42 may be disposed about one another to provide a variety of flexibility, hardness, and/or stiffness characteristics as desired. As such the secondary tubular member may be constructed of any of a wide variety of materials including, but not limited to, metal(s), polymer(s), natural rubber, silicone, multilayer materials, urethanes, PEBAX, HDPE, etc.

In the illustrative embodiment, stent 36 may be disposed about at least a portion of balloon 14 and/or secondary tubular member 42. As illustrated, a proximal portion of stent 36 may be disposed about both the balloon 14 and the secondary tubular member 42 and a distal portion of the stent may be disposed about only the balloon 14. In this configuration, a distal end of the secondary tubular member 42 may extend through an intermediate opening of the stent 36. In the illustrative example, the intermediate opening of the stent 36 may be provided at any suitable location between a distal end and a proximal end of the stent 36, as desired.

In some cases, stent 36 may be at least partially constructed of a plurality of interconnected struts, connectors, or other members. The stent 36 defines a proximal opening, a distal opening, and a flow path therebetween. The intermediate opening may also be in fluid communication with the flow path, if desired. In some embodiments, the stent 36 may be a standard "single vessel" stent that is provided with an intermediate opening in the manner described above, or the stent 36 may also be a bifurcated stent having a trunk and/or stem portion, with one or more leg portions and/or branch openings adjacent thereto, through which the secondary guidewire may be passed. Such bifurcated stents and stent assemblies are well known in the art. Furthermore, it is contemplated that the stent 36 may be a standard single vessel stent with no intermediate opening or any other suitable stent, as desired. In some situations, it is contemplated that the catheter may not include the secondary tubular member 42, if desired.

In the illustrative embodiment, guidewire 38 may be slidably disposed through a lumen of the elongate member 11. As illustrated, the guidewire 38 may be disposed in a first port at the distal end of the catheter 10 and through a second port 24 shown in the midshaft 18. In some cases, guidewire port 24 may be provided distally of the actuatable junction 22. For example, guidewire port 24 may be provided in the midshaft 18 of the elongated member 11 or in the distal section 20 of the elongated member 11, as desired. However, this is not meant to be limiting. It is contemplated that the second port 24 may be disposed proximally of the actuatable junction 22, as desired.

In the illustrative embodiment, guidewire 40 may be slidably disposed through the lumen of the secondary tubular member 42. However, in some cases, the guidewire 40 may be merely slid between the balloon 14 and the stent 36 without the use of the secondary tubular member 42. In some embodiments, where the stent 36 is to be positioned substantially proximal to a side branch of the bifurcation, the guidewire 40 and/or secondary tubular member 42 may be configured to extend under the entire length of the stent 36.

In the illustrative dual guidewire embodiment, in operation, the guidewire 38 may be initially advanced through a vessel distal of a side branch of a bifurcation and the secondary guidewire 40 may be advanced through the vessel and into the side branch of the bifurcation. The catheter 10 may then be advanced along the guidewires 38 and 40 through the vessel until the balloon 14 and the stent 36 reach a desired position in the vessel, such as, for example, adjacent to the side branch of the bifurcation. While advancing the catheter 10 over the guidewires 38 and 40, the actuatable junction 22 may be in a rotatable and/or non-fluidly sealed state allowing at least in part the portion of the catheter 10 distal of the actuatable junction 22 may be configured to rotate relative to the portion of the catheter 10 proximal to the actuatable junction 22. In particular, the catheter 10 may be advanced over crossed or otherwise twisted guidewires 38 and 40. In addition, the balloon 14 and stent 36 may be rotated to align the intermediate opening of the stent 36 with the side branch vessel at the bifurcation while being advanced over the guidewires 38 and 40. Once properly positioned, the actuatable junction 22 may be actuated to a fluidly sealed and/or rotatably fixed state, as described previously. In some cases, inflating the balloon 14 may deploy the stent 36. However, any other suitable deployment may be used, as desired.

In at least some embodiments, portions or all of catheter 10, or other components that are part of or used in the device, may be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of catheter 10 to achieve the same result.

In some embodiments, a degree of MRI compatibility is imparted into catheter 10. For example, to enhance compatibility with Magnetic Resonance Imaging (MRI) machines, it may be desirable to make hypotube 17, midshaft 18, distal section 20, and/or inflatable balloon 14, or other portions of the medical device 10, in a manner that would impart a degree of MRI compatibility. For example, hypotube 17, midshaft 18, distal section 20, and/or inflatable balloon 14, or portions thereof, may be made of a material that does not substantially distort the image and create substantial artifacts (artifacts are gaps in the image). Certain ferromagnetic materials, for example, may not be suitable because they may create artifacts in an MRI image. Hypotube 17, midshaft 18, distal section 20, and/or inflatable balloon 14, or portions thereof, may also be made from a material that the MRI machine can image. Some materials that exhibit these characteristics include, for example, tungsten, Elgiloy, MP35N, nitinol, and the like, and others.

In some embodiments, a sheath and/or coating, for example a lubricious, a hydrophilic, a protective, or other type of material may be applied over portions or all of the hypotube 17, midshaft 18, distal section 20, and/or inflatable balloon 14, or other portions of device 10. Some examples of suitable polymer sheath materials may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In some embodiments sheath material can be blended with a liquid crystal polymer (LCP). For example, the mixture can contain up to about 6% LCP. This has been found to enhance torqueability. By employing selection of materials and processing techniques, thermoplastic, solvent soluble, and thermosetting variants of these and other materials can be employed to achieve the desired results. Some examples of suitable coating materials may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Some coating polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

A coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

In some cases, hypotube 17, midshaft 18, and/or distal section 20 can be made of the same material along its length, or in some embodiments, can include portions, sections, or layers made of different materials. In some embodiments, the material used to construct hypotube 17, midshaft 18, and/or distal section 20 are chosen to impart varying flexibility, torqueability, and stiffness characteristics to different portions of hypotube 17, midshaft 18, and/or distal section 20.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. For example, although set forth with specific reference to catheters in some of the example embodiments shown in the Figures and discussed above, the invention may relate to virtually any medical device that may aid a user of the device in advancing a device in a vessel. For example, the invention may be applied to medical devices such as a guidewire, a balloon catheter, an atherectomy catheter, a drug delivery catheter, a stent delivery catheter, an endoscope, a fluid delivery device, other infusion or aspiration devices, delivery (i.e. implantation) devices, and the like. Thus, while the Figures and descriptions above are directed toward a guidewire, in other applications, sizes in terms of diameter, width, and length may vary widely, depending upon the desired properties of a particular device. The scope of the invention is, of course, defined in the language in which the appended claims are expressed.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device comprising:
    a first elongated member having a proximal end, a distal end, and a lumen extending therebetween;
    a second elongated member having a proximal end, a distal end, and a lumen extending therebetween, wherein the proximal end of the second elongated member is disposed adjacent to the distal end of the first elongated member forming a junction; and
    a seal disposed adjacent to the first elongated member and the second elongated member at the junction, the seal being actuatable between a first state and a second state while the first and second elongated members are connected at the junction, wherein, in the first and second states, the first elongated member is rotatable relative to the second elongated member and, in the first state, the first elongated member is non-fluidly sealed to the second elongated member and, in the second state, the first elongated member is fluidly sealed to the second elongated member, wherein the lumen of the second elongated member defines, at least in part, one or more guidewire lumens, wherein the guidewire lumen has a distal port adjacent to the distal end of the second elongated member and a proximal port, wherein the proximal port is distal of the junction.

2. The medical device of claim 1 wherein the seal is actuatable between the first state and second state by a pressure.

3. The medical device of claim 2 wherein the pressure is provided by a fluid flowing through the lumen of the first elongated member and/or the second elongated member.

4. The medical device of claim 1 wherein the seal is electrically actuated between the first state and the second state.

5. The medical device of claim 4 wherein the seal includes an electroactive polymer that is configured to expand and/or contract in response to an electrical potential.

6. The medical device of claim 1 wherein the second elongated member includes an inflatable balloon adjacent to the distal end, wherein the balloon is fluidly connected to the proximal end of the first elongated member.

7. The medical device of claim 6 further comprising a stent disposed about at least a portion of the balloon.

8. The medical device of claim 7 wherein the stent is a bifurcated stent.

9. A medical device comprising:
   a first elongated member having a proximal end, a distal end, and a lumen extending therebetween;
   a second elongated member having a proximal end, a distal end, and a lumen extending therebetween, wherein one of the proximal end or the distal end of the second elongated member is disposed within at least a portion of the lumen of the first elongated member;
   a first and second retainer disposed on an inner surface of the first elongated member with the lumen of the first elongated member;
   a third retainer disposed on an outer surface of the second elongated member, wherein the third retainer is disposed longitudinally between the first and second retainer; and
   wherein the first retainer, second retainer, and/or third retainer form a seal that is actuatable between a first state and a second state while the first and second elongated members are connected, wherein when in the first and second states, the first elongated member is rotatable relative to the second elongated member and, when in the first state, the first elongated member is non-fluidly sealed to the second elongated member and, when in the second state, the first elongated member is fluidly sealed to the second elongated member, wherein the seal is actuated by longitudinally moving the first and second elongate members away from each other.

10. The medical device of claim 9 wherein the seal is actuatable between the first state and second state by a pressure.

11. The medical device of claim 10 wherein the pressure is provided by a fluid flowing through the lumen of the first elongated member and/or the second elongated member.

12. The medical device of claim 9 wherein the seal is electrically actuated between the first state and the second state.

13. The medical device of claim 12 wherein at least one of the first retainer, second retainer, and third retainer includes an electroactive polymer that is configured to expand and/or contract in response to an electrical potential.

14. The medical device of claim 9 wherein the second elongated member includes one or more guidewire lumens disposed therein, wherein the guidewire lumen includes a distal port and a proximal port, wherein the proximal port is distal of the seal.

15. The medical device of claim 9 wherein the third retainer and at least one of the first retainer and second retainer interlocks.

16. The medical device of claim 9 wherein the seal formed by the first retainer, second retainer, and/or third retainer is a friction fit seal.

17. A catheter comprising:
   a first elongated member having a proximal end, a distal end, and a lumen extending therebetween;
   a second elongated member having a proximal end, a distal end, and a lumen extending therebetween, wherein the proximal end of the second elongated member is disposed adjacent to the distal end of the first elongated member forming a junction, and the distal end of the second elongated member has an inflatable balloon disposed thereon; and
   a seal disposed adjacent to the first elongated member and the second elongated member at the junction, the seal being actuatable between a first state and a second state by a fluidic pressure while the first and second elongated members are connected at the junction, wherein the first elongated member is rotatable relative to the second elongated member in the first and second states, and, in the first state, the first elongated member is non-fluidly sealed to the second elongated member, and, in the second state, the first elongated member is fluidly sealed to the second elongated member.

18. The catheter of claim 17 wherein the distal end of second elongated extends distally of the distal end of the first elongated member.

19. The catheter of claim 17 wherein the second elongated member includes a proximal port and a distal port with a second lumen extending therebetween, wherein the proximal port is distal of the junction.

20. The catheter of claim 19 wherein the second lumen is a guidewire lumen.

21. The catheter of claim 17, wherein the seal limits longitudinal movement of the first and second elongated members relative to each other in the first and second states.

* * * * *